United States Patent [19]

Ward et al.

[11] Patent Number: 5,212,163
[45] Date of Patent: May 18, 1993

[54] COMPOUNDS

[75] Inventors: Robert W. Ward; Roger E. Markwell; David J. Hunter, all of Harlow, England

[73] Assignee: Beecham Group p.l.c., Middlesex, England

[21] Appl. No.: 758,356

[22] Filed: Sep. 9, 1991

Related U.S. Application Data

[63] Continuation of Ser. No. 508,272, Apr. 11, 1990, abandoned.

[30] Foreign Application Priority Data

Apr. 13, 1989 [GB] United Kingdom ............... 8908353
Aug. 3, 1989 [GB] United Kingdom ............... 8917756

[51] Int. Cl.$^5$ ............... A61K 31/675; A61K 31/66; C07K 5/02; C07K 5/06
[52] U.S. Cl. ............... 514/80; 514/79; 514/114; 540/451; 540/487; 548/413; 558/190
[58] Field of Search ............... 558/190; 540/451, 487; 548/413; 514/79, 80, 114

[56] References Cited

U.S. PATENT DOCUMENTS 4,558,034 12/1985 Galardy et al. ............... 514/7
4,935,404 6/1990 Hunter et al. ............... 514/19

Primary Examiner—Robert T. Bond
Attorney, Agent, or Firm—Hopgood, Calimafde, Kalil, Blaustein & Judlowe

[57] ABSTRACT

Novel compounds of formula (I) and salts, solvates and hydrates thereof, processes for their preparation and their use in the treatment of conditions in which degradation of connective tissue and other proteinaceous components of the body occurs:

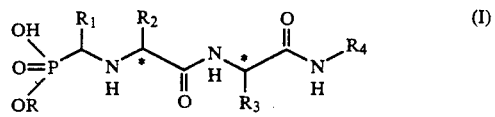

in which, R is hydrogen, $C_{1-6}$ alkyl or optionally substituted benzyl; $R_1$ is hydrogen or $C_{1-6}$ alkyl; $R_2$ is $C_{3-6}$ alkyl; $R_3$ is hydrogen, alkyl, —$CH_2$—Z where Z is optionally substituted phenyl or heteroaryl, or $R_3$ is a group

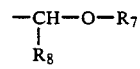

where $R_7$ is hydrogen, alkyl or —$CH_2$—Ph where Ph is optionally substituted phenyl and $R_8$ is hydrogen or alkyl; and $R_4$ is —$CH_2$—$(CH_2)_n OR_5$ or —$CH_2$—$(CH_2)_n OCOR_6$ or —$CH(R_9)COR_{10}$, where n is an integer from 1 to 6; $R_5$, $R_6$ and $R_9$ are hydrogen or $C_{1-6}$ alkyl; and $R_{10}$ is hydroxy or —O—$C_{1-6}$ alkyl or —$NR_5R_6$ (where $R_5$ and $R_6$ may be linked to form a heterocyclic ring; or $R_3$ and $R_4$ are joined together as —$(CH_2)_m$— where m is an integer from 4 to 12.

15 Claims, No Drawings

COMPOUNDS

This application is a continuation of application Ser. No. 508,272, filed Apr. 11, 1990, now abandoned.

The present invention relates to novel phosphorus derivatives, processes for their preparation and their use in medicine. In particular, the present invention relates to their use as inhibitors of enzymes of the collagenase family of neutral metalloproteases, for treating arthritic and other diseases.

The mammalian collagenase family of enzymes comprises a number of proteases, exemplified by interstitial (type I) collagenase itself, the stromelysins (also known as proteoglycanases or transins), fibroblast and polymorphonuclear leucocyte gelatinases (also known as collagen-IV-ases), and 'pump-1' (putative metalloprotease 1, uterine metalloprotease) [Goldberg et al., J. Biol. Chem. 2610, 6600, 1986; Whitham et al., Biochem. J. 240. 913, 1986; Breathnach et al., Nucleic Acids Res., 15, 1139, 1987; Muller et al., Biochem. J., 253, 187, 1988; Collier et al., J. Biol. Chem., 263, 6579, 1988; Murphy et al., Biochem. J., 258, 463, 1989; Quantin et al., Biochem. (N.Y.), 28, 5327, 1989; Birkedal-Hansen, J. Oral Pathol., 17, 445, 1988]. Membership of the mammalian collagenase family of proteases is evident by possession of a number of highly characteristic and experimentally verifiable properties, which can be adopted as criteria for allocation to this family of enzymes, selected from the following:

(a) Optimal proteolytic activity around neutral pH.

(b) Dependence of the enzyme's activity on the presence of zinc, as evident by the loss of activity on treatment with divalent metal ion chelators, such as 1,10 phenanthroline (preferential chelation of zinc), or EDTA (less restricted chelating properties; EDTA and EGTA also contribute to enzyme inactivation via chelation of calcium ions required for enzyme stability.)

(c) Inhibition by TIMP (Tissue Inhibitor of Metalloproteases), a proteinaceous inhibitor thought to play a significant role in the physiological control of the collagenase family of enzymes. Other families of metalloproteases are not inhibited by TIMP, at least as far as the relevant studies have so far been pursued.

(d) Absence of significant inhibition by known inhibitors of other families of neutral, zinc-containing metalloproteases, such as thermolysin, angiotensin-converting enzyme and 'enkephalinase' (EC 3.4.24.11). One of the inhibitors most often used is phosphoramidon, which inhibits thermolysin and enkephalinase.

(e) Biosynthesis and secretion as latent precursor forms (zymogens), requiring extracellular activation. Activation has been achieved by a number of endoproteases, organomercurials and chaotropic agents.

Members of the collagenase family of neutral metalloprotease enzymes have distinctive substrate specificities. Thus, collagenase type I itself is unique in its ability to cleave a specific peptide bond within the native fibrils of the interstitial collagens (e.g. types I, II and III). The gelatinases are only poorly active on these collagens, but are able to degrade denatured interstitial collagens, as well as the non-fibrillar collagens, e.g. type IV, such as are found in the basement membrane. Pump-1 has been reported to act preferentially on denatured collagens (gelatins), though its profile differs from that of the stromelysins or the collagenases type IV. Both the stromelysins and the gelatinases are also capable of degrading non-collagenous structural proteins, such as the core protein of proteoglycan and elastin. Macromolecules involved in cell-to-substratum and cell-to-cell interactions, such as laminin and fibronectin, are also susceptible to degradation by several of these metalloproteases.

The range of therapeutic applications of the inhibitors of the collagenase family of enzymes described hereinafter reflects the fundamental role of these and other proteinaceous substrates of these enzymes in the connective tissue matrix throughout the body. Applications extend to clinical interventions in many diseases and phenomena not primarily due to a net destruction of collagen and other connective tissue components, but involving normal or disordered tissue remodelling.

Enzymes of the collagenase family are produced by synovial and skin fibroblasts, chondrocytes, peripheral mononuclear cells, keratinocytes and gingival tissue, as well as existing within granular storage vesicles in polymorphonuclear leucocytes (PMNLs).

Inhibitors of the collagenase family of enzymes are considered to provide useful treatments for:

(i) arthritic diseases, such as rheumatoid and osteo-arthritis, soft tissue rheumatism, polychondritis and tendonitis;

(ii) bone resorption diseases, such as osteoporosis, Paget's disease, hyperparathyroidism and cholesteatoma;

(iii) the enhanced collagen destruction that occurs in association with diabetes;

(iv) the recessive classes of dystrophic epidermolysis bullosa;

(v) periodontal disease and related consequences of gingival production of collagenase, or of PMNL collagenase release following cellular infiltration to inflamed gingiva, including by combating the greater susceptibility of diabetes patients to periodontal disease;

(vi) corneal ulceration, e.g. that induced by alkali or other burns, by radiation, by vitamin E or retinoid deficiency;

(vii) ulceration of the skin and gastro-intestinal tract, and abnormal wound healing;

(viii) post-operative conditions, including colonic anastomosis, in which collagenase levels are raised;

(ix) cancer, where members of the collagenase family of enzymes have been implicated in the neovascularization required to support tumour growth and survival, in the tissue remodelling required to accommodate the growing primary and secondary tumours, and in the penetration of tumour cells through the basement membrane of the vascular walls during metastasis;

(x) demyelinating diseases of the central and peripheral nervous systems, including syndromes in which myelin loss is the primary pathological event and those in which demyelination follows axonal atrophy. The degradation of myelin in these diseases, exemplified by multiple sclerosis, is mediated by members of the collagenase family of enzymes.

As a particular example of the therapeutic value of inhibitors of the collagenase family of enzymes such as are disclosed in the present invention, chronic arthritic diseases leading to extensive loss of the collagen, proteoglycan and elastin components of the cartilage, bone and tendons within the joints, should be amenable to treatment with inhibitors of the collagenases, proteoglycanases (stromelysins) and gelatinases currently thought to be the major enzymes involved.

These enzymes have been detected in extracts of synovial and cartilage tissue, and have also been extensively studied in tissue cultures of a wide range of connective tissues. Apart from control of the biosynthesis, secretion and activation of the enzymes, the most important natural regulation of these enzymes in normal and diseased states, is considered to be the endogenous production of inhibitors such as the Tissue Inhibitor of Metalloproteases, and alpha-2 macroglobulin. An imbalance between the local levels of the proteolytic enzymes and natural inhibitors will allow destruction of connective tissue components to occur.

The compounds described in the present invention, being synthetic and low molecular weight inhibitors of this family of enzymes, offer a therapeutically useful way in which a more normal or non-pathological balance between inhibition and enzymic activity can be restored: they thus act to complement and supplement the endogenous enzyme inhibitors. Indeed, because these enzymes usually act only within restricted pericellular environments, before being inactivated by inhibitors circulating in the blood and present in most inflammatory exudates, the low molecular weight inhibitors disclosed here may be more effective than endogenous proteinaceous inhibitors that are excluded by their size from the localized regions of connective tissue destruction.

European Patent 0054862 discloses a class of substituted dipeptides having useful enkephalinase inhibiting activity.

Novel structurally related compounds have now been discovered, which are collagenase inhibitors and thus of potential utility in the treatment of diseases in which collagenolytic activity and tissue remodelling is implicated.

According to the present invention there is provided a compound of general formula (I), or a salt, solvate or hydrate thereof:

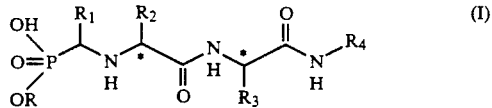

in which,

R is hydrogen, $C_{1-6}$ alkyl or optionally substituted benzyl;

$R_1$ is hydrogen or $C_{1-6}$ alkyl;

$R_2$ is $C_{3-6}$ alkyl;

$R_3$ is hydrogen, alkyl, —$CH_2$—Z where Z is optionally substituted phenyl or heteroaryl, or $R_3$ is a group

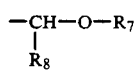

where $R_7$ is hydrogen, alkyl or —$CH_2$—Ph where Ph is optionally substituted phenyl and $R_8$ is hydrogen or alkyl; and $R_4$ is —$CH_2$—$(CH_2)_n OR_5$ or —$CH_2$—$(CH_2)_n OCOR_6$ or

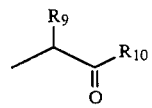

where n is an integer from 1 to 6; $R_5$, $R_6$ and $R_9$ are hydrogen or $C_{1-6}$ alkyl; and $R_{10}$ is hydroxy or —O—$C_{1-6}$ alkyl or —$NR_5R_6$ (where $R_5$ and $R_6$ may be linked to form a heterocyclic ring);

or $R_3$ and $R_4$ are joined together as —$(CH_2)_m$— where m is an integer from 4 to 12.

Unless otherwise specified, each alkyl group is preferably a $C_{1-8}$ group, more preferably $C_{1-6}$, and may be a straight chain or branched.

Optional substituents for phenyl and heteroaryl groups may be selected from OH, $C_{1-6}$ alkyl, $C_{1-6}$ alkoxy, halogen, —NHCO $C_{1-6}$ alkyl, —NHCOPh and —$CONR_5R_6$, where Ph, $R_5$ and $R_6$ are as defined above.

The term optionally substituted benzyl when used herein means a benzyl group in which the phenyl moiety is optionally substituted. Optional substituents include those hereinbefore defined for phenyl and heteroaryl groups in relation to variable $R_3$.

Z when heteroaryl includes 5- or 6-membered monocyclic and 9- or 10-membered bicyclic heteroaryl.

In addition, 5- or 6-membered monocyclic and 9- or 10-membered bicyclic heteroaryl preferably contain one or two heteroatoms selected from nitrogen, oxygen and sulphur. When Z is 9- or 10- membered bicyclic heteroaryl the two rings are fused with one 5- or 6-membered ring preferably containing a single heteroatom, for example indolyl.

R is preferably hydrogen, methyl or ethyl, especially hydrogen.

Values for $R_1$ include hydrogen, methyl, ethyl, isopropyl and n-butyl. As an alkyl group, $R_1$ is preferably methyl or ethyl.

$R_2$ is preferably a $C_4$ alkyl group, such as n-butyl, iso-butyl or sec-butyl, especially iso-butyl.

$R_3$ is preferably benzyl, 4-hydroxybenzyl, $C_{1-6}$ alkoxybenzyl such as 4-methoxybenzyl or 9- or 10-membered fused bicyclic heteroarylmethyl such as 3-indolylmethyl.

Values for $R_4$ include —$(CH_2)_2OCH_3$, —$CH(CH_3)CO_2CH_3$, and —$(CH_2)_2OH$.

Preferably groups $R_3$ and $R_4$ are combined as —$(CH_2)_m$. An especially favourable form is where $m = 10$, resulting in a lactam structure based on a 13-membered ring.

The compounds of formula (I) may form salts with bases e.g. sodium hydroxide. The compounds of formula (I) have a basic nitrogen atom and may form acid addition salts e.g. with hydrochloric acid. Such compounds form part of the present invention.

Where compounds of formula (I), or salts thereof, form solvates or hydrates, these also form an aspect of the invention.

The compounds of formula (I) have at least one, and may have two, three or more asymmetric centres and therefore exist in more than one stereoisomeric form. The invention extends to all such forms and to mixtures thereof, including racemates, and diastereoisomeric mixtures.

Preferred isomers are those having the S configuration at the chiral centres marked with an asterisk in formula (I), when $R_3$ is other than hydrogen.

The compounds of formula I or their salts, solvates or hydrates are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels.

The compounds of formula (I) or their salts, solvates or hydrates are preferably in substantially pure form. A substantially pure form will generally contain at least 50% by weight, preferably 75%, more preferably 90% and still more preferably 95% or 99% or more of the compound of formula I or its salt or solvate.

Compounds of formula (I) or their salts, solvates or hydrates may be isolated as crystalline solids or in the form of foams or gums.

A preferred pharmaceutically acceptable form is the crystalline form.

The present invention provides the compounds of formula (I) or pharmaceutically acceptable salts thereof for use as active therapeutic agents, particularly as agents for treatment of conditions in which degradation of connective tissue and other proteinaceous components of the body occurs, such as musculo-skeletal disorders resulting from collagenolytic activity, particularly rheumatism and/or arthritic conditions, and tissue remodelling.

Compounds of formula (I) also have potential utility in the treatment of cancer; for preventing myelin degradation in the central and peripheral nervous system; and in other conditions in which members of the collagenase family of neutral metalloproteases have pathological or other roles.

The present invention also provides a process for the preparation of a compound of formula (I) which comprises converting a group $R_{20}$ to hydrogen by cleaving a group $R_{20}$ from a compound of formula (II):

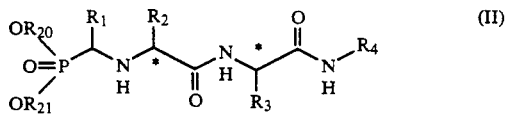

wherein $R_{20}$ is alkyl or optionally substituted benzyl and $R_{21}$ is hydrogen or alkyl or optionally substituted benzyl and $R_1$, $R_2$, $R_3$ and $R_4$ are as defined in formula (I), and where necessary, converting $R_{21}$ to hydrogen.

Cleavage of $R_{20}$, and where necessary $R_{21}$, may be carried out in aqueous acid or alkali or using a trimethylsilyl halide, preferably bromotrimethylsilane, in an inert solvent, for example dichloromethane. Benzyl esters may alternatively be removed by hydrogenolysis or other standard debenzylation procedures.

When both $R_{20}$ and $R_{21}$ are alkyl, cleavage of $R_{20}$ only, to give to a compound of formula (II) in which $R_{20}$ is hydrogen and $R_{21}$ alkyl, which is a compound of formula (I) in which R is alkyl, may be carried out by treatment with excess alkali under mild conditions, for example with aqueous sodium hydroxide in an alcoholic solvent at room temperature.

Similarly, where $R_{20}$ is optionally substituted benzyl and $R_{21}$ is alkyl, the benzyl group only may be cleaved by hydrogenation to give a compound of formula (II) in which $R_{20}$ is hydrogen and $R_{21}$ is alkyl.

Cleavage of an $R_{21}$ alkyl group may thereafter be carried out as described above to give a compound of formula (I) in which R is hydrogen.

When R in a compound of formula (I) is hydrogen and $R_{21}$ in a compound of formula (II) is not hydrogen, then cleavage of both $R_{21}$ and $R_{20}$ is conveniently effected in a single reaction. Preferably $R_{20}$ and $R_{21}$ are both alkyl, such as methyl or ethyl, or benzyl.

It will be appreciated that compounds of formula (II) in which $R_{21}$ is hydrogen are themselves compounds of the invention of formula (I).

Compounds of formula (II) may be prepared by treating a compound of formula (III):

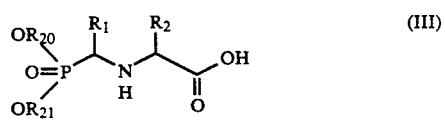

in which $R_1$, $R_2$, $R_{20}$ and $R_{21}$ are as defined in formula (II) (except that $R_{21}$ is not H), with a compound of formula (IV):

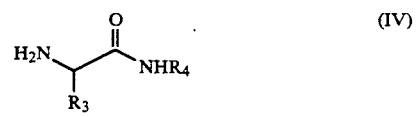

in which $R_3$ and $R_4$ are as defined in formula (I).

The reaction is preferably carried out in the presence of a coupling agent, such as dicyclohexylcarbodiimide or 1-ethyl-3-[3-(dimethylamino)propyl]carbodiimide hydrochloride in the presence of 1-hydroxybenzotriazole, or using 1,1'-carbonyldiimidazole, in an inert solvent such as dichloromethane or acetonitrile.

Selective cleavage of the group $R_{21}$ may then be carried out using the procedures described above for the preparation of compounds of formula (I) to give compounds of formula (II) which $R_{21}$ is hydrogen.

The intermediate compounds of formula (III) may be prepared by treating a compound of formula (V) or a salt thereof:

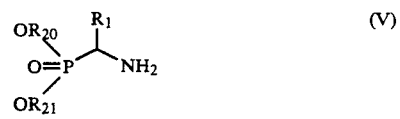

in which $R_1$, $R_{20}$ and $R_{21}$ are as defined in formula (III), with a compound of formula (VIA) or (VIB) or a salt thereof:

in which $R_2$ is as defined in formula (I), $R_{11}$ is a leaving group such as halogen, methanesulphonyloxy or trifluoromethanesulphonyloxy and $R_{12}$ is hydrogen or a carboxyl protecting group, and thereafter removing an $R_{12}$ carboxyl protecting group.

When a compound of formula (VIB) is used, the reductive amination may be carried out by hydrogenation over a noble metal catalyst such as palladium on carbon or by reaction with sodium cyanoborohydride at pH 6 to 7. Lower alkyl alcohol solvents such as methanol and ethanol are suitable for both reactions. These reactions may be carried out in the presence of molecular sieves.

A hydrogenation reaction is preferred but this process precludes the use of compounds of formulae (V) and (VIB) in which any of $R_{20}$, $R_{21}$ or $R_{12}$ is benzyl. Preferably a carboxyl protecting group is a methyl or ethyl ester. Ester protecting groups may be removed under standard basic hydrolysis conditions using dilute base such as 1 Normal aqueous sodium hydroxide in methanol.

When the compound of formula (V) is in the form of the free base, the compound of formula (VIB) is suitably an $\alpha$-keto ester ($R_{12}$=alkyl).

When the compound of formula (V) is a salt, such as the hydrochloride salt, the compound of formula (VIB) is suitably a salt of an $\alpha$-keto acid ($R_{12}$=H), for example the sodium salt.

The preparation of compounds of formula (III) using a compound of formula (VIA) may be carried out under standard alkylation conditions. A halogen leaving group is preferably bromine and an oxygen-based leaving group is preferably trifluoromethanesulphonyloxy.

Compounds of formula (III) may alternatively be prepared by condensing a compound of formula (VII) or a salt thereof:

in which $R_2$ is as defined in formula (I) and $R_{12}$ is a carboxyl protecting group with an aldehyde, $R_1$—CHO in which $R_1$ is as defined in formula (I) and treating the condensation product with an appropriate dialkyl or trialkyl phosphite, for example dimethyl phosphite, and thereafter removing the carboxyl protecting group. The carboxyl group is conveniently protected as an alkyl or benzyl ester which may be removed using standard hydrolysis or hydrogenation conditions.

As described above in connection with reductive amination of compounds of formula (VIB), where a benzyl protecting group $R_{12}$ is removed by hydrogenation then $R_{20}$ and $R_{21}$ are restricted to alkyl Alternatively, compounds of formula (II) in Which $R_{20}$ and $R_{21}$ are alkyl or optionally substituted benzyl may be prepared by the reaction of a compound of formula (VIII):

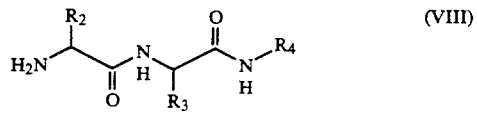

in which $R_2$, $R_3$ and $R_4$ are as defined in formula (I), with a compound of formula (IX):

in which $R_1$ is as defined in formula (I), $R_{20}$ and $R_{21}$ are alkyl or optionally substituted benzyl and $R_{11}$ is a leaving group as defined for formula (VIA), in the presence of a base such as triethylamine or Proton Sponge (1,8-bis(dimethylamino)-naphthalene), or using anhydrous potassium carbonate in an alcoholic solvent.

Where $R_{11}$ is an oxygen-based leaving group, for example trifluoromethanesulphonyloxy, which is preferred, displacement of the leaving group is conveniently carried out in the presence of Proton Sponge in an inert solvent such as methanol, over a period of several days in the absence of light.

A further alternative preparation of compounds of formula (III) may be carried out by reacting a compound of formula (IX) as hereinbefore defined with a compound of formula (VII) in which $R_{12}$ is a carboxyl protecting group, using conditions as described for the reaction of compounds of formula (VIII) with compounds of formula (IX), and thereafter removing the protecting group $R_{12}$.

Suitable carboxyl protecting groups include alkyl, benzyl and trialkylsilyl groups. A trialkylsilyl protecting group, for example trimethylsilyl, is especially useful in that it may be readily incorporated, in situ, for example by addition of hexamethyldisilazane to the reactants in acetonitrile in the presence of triethylamine, and selectively removed in aqueous methanol, without imposing any limitations on the value of $R_{20}$ and $R_{21}$. Other silylating agents include trimethylsilyl chloride and N,N-diethyltrimethylsilylamine.

An $R_{12}$ alkyl carboxyl protecting group may be removed by base hydrolysis, for example using sodium hydroxide in aqueous methanol.

It will be appreciated that where the carboxyl protecting group $R_{12}$ is alkyl, $R_{20}$ and $R_{21}$ may be alkyl or benzyl derivatives, but where $R_{12}$ is a benzyl group, $R_{20}$ and $R_{21}$ are limited to alkyl.

When compounds of formula (III) are prepared by this route, it is preferred that $R_{20}$ and $R_{21}$ are benzyl and $R_{11}$ is trifluoromethanesulphonyloxy in the compound of formula (IX) and $R_{12}$ is trimethylsilyl or methyl in the compound of formula (VII).

Compounds of formula (VIII) may be prepared by treating a compound of formula (VII):

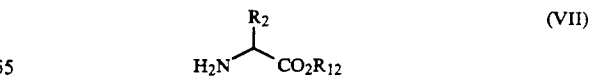

in which $R_2$ is as defined in formula (I), $R_{12}$ is hydrogen and wherein the amino group is optionally protected, with a compound of formula (IV) as hereinbefore defined, in the presence of a coupling agent as hereinbefore described for the preparation of compounds of formula (II) from compounds of formulae (III) and (IV).

Compounds of formula (IX) may be prepared from hydroxyalkylphosphonate derivatives by conversion of the hydroxyl group to the leaving group $R_{11}$ by conventional methods. For example, where $R_{11}$ is trifluoromethanesulphonyloxy, trifluoromethanesulphonic anhydride may be added to a solution of the hydroxyalkylphosphonate in an inert solvent such as dichloromethane, the reaction being carried out at reduced temperature under an inert atmosphere, according to the general method of E. Vedejs et al., Journal of Organic Chemistry 50, 2165, (1985).

Hydroxyalkylphosphonate compounds may in turn be prepared by reaction of the corresponding phosphite, for example dibenzylphosphite, with an aldehyde $R_1$—CHO in which $R_1$ is as defined in formula (I) according to the general method of F. Texier-Boullet and A. Foucaud, Synthesis, 916 (1982). Benzyl and alkyl phosphites are either commercially available compounds or can be prepared from commercially available starting materials by standard methods.

Intermediate compounds of formula (V) are either known compounds or may be prepared from known aminoalkyl phosphonic acid derivatives using standard procedures to introduce $R_{20}$ and $R_{21}$ as required.

Protection of the amine function during these reactions may be necessary.

Introduction of an $R_{20}$ or $R_{21}$ methyl group may be effected by reaction with diazomethane in a suitable inert solvent.

Compounds of formula (V) of fixed configuration may be prepared by the general method of R. Jacquier et al., Phosphorus and Sulfur 36, 73, (1988).

The compounds of formulae (IV) and (VII) are either known amino acid derivatives or can be made from these derivatives by known methods. Compounds of formula (VIA) and (VIB) are either known compounds or may be prepared from known compounds by known methods.

The intermediates of formulae (II), (III), and certain intermediates of formula (V) disclosed herein are novel compounds and form an aspect of the present invention as do the described processes for their preparation.

Where obtainable, pharmaceutically acceptable salts of the compounds of formula (I) may be formed conventionally by reaction with the appropriate acid or base. Solvates may be formed by crystallization from the appropriate solvent.

As mentioned previously, the compounds of formula (I) exist in more than one diastereoisomeric form. Where the processes of the invention produce mixtures thereof, the individual isomers may be separated one from another by chromatography e.g. HPLC.

Alternatively, separate diastereoisomeric compounds of formula (I) can be obtained by using stereoisomerically pure starting materials or by separating desired isomers of intermediates at any stage in the overall synthetic process, and converting these intermediates to compounds of formula (I).

It will be appreciated that where a single diastereoisomer of a compound of formula (I) is prepared by more than one process variant as hereinbefore described, each of which allows a different chiral centre to be defined, it may be possible to deduce the configuration at a chiral centre which is not pre-determined using a particular process variant.

Furthermore, it will be appreciated that although the absolute configuration at a particular chiral centre may not be known, it is possible to characterise a given diastereoisomer relative to its epimer by reference to the direction in which the plane of polarised light is rotated.

The present invention further provides a pharmaceutical composition, which comprises a compound of formula (I), or a pharmaceutically acceptable salt or solvate thereof, and a pharmaceutically acceptable carrier.

A composition of this invention is useful in the treatment of musculo-skeletal disorders, particularly arthritic diseases and for modulation of tissue remodelling.

A composition of the invention also has potential utility in the treatment of cancer; for preventing myelin degradation in the central and peripheral nervous system; and in other conditions in which members of the collagenase family of neutral metalloproteases have pathological or other roles.

A composition of the invention, which may be prepared by admixture, may contain a diluent, binder, filler, disintegrant, flavouring agent, colouring agent, lubricant or preservative in conventional manner. These conventional excipients may be employed in conventional manner, for example as in the preparation of compositions of related peptide enzyme inhibitors, such as the ACE inhibitor enalapril.

A composition of the invention may be adapted for oral, topical, rectal or parenteral administration but oral administration is preferred. Parenteral compositions may be administered intravenously, intramuscularly or intra-articularly.

Preferably, a pharmaceutical composition of the invention is in unit dosage form and in a form adapted for use in the medical or veterinarial fields. For example, such preparations may be in a pack form accompanied by written or printed instructions for use as an agent in the treatment or prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen.

The compound or composition of the invention may be formulated for administration by any route, the preferred route depending upon the disorder for which treatment is required, and is preferably in unit dosage form or in a form that a human patient may administer to himself in a single dosage.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

Solid compositions may be obtained by conventional methods of blending, filling, tableting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients. For example, in a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository or for parenteral administration in an injectable form. For injection, for example by intra-articular injection or by injection into the cerebro-spinal fluid or via other routes which will gain access to sites of demyelination, as freely soluble solutions or as poorly dispersed depot stores, the compounds of the invention may be presented in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers or solutes to render the solution isotonic with the blood, thickening agents, suspending agents or other pharmaceutically acceptable additives. Such forms will be presented in sterile unit dose form such as ampoules or disposable injection devices or in multi-dose forms such as a bottle from which the appropriate dose may be withdrawn or a solid form or concentrate which can be used to prepare an injectable formulation.

For topical and percutaneous administration, the preparations may also be presented as an ointment, cream, lotion, gel, spray, aerosol, wash, skin paint or patch.

A unit dose for inflammatory diseases will generally contain from 10 to 1000 mg and preferably will contain from 10 to 500 mg, in particular 10, 50, 100, 150, 200, 250, 300, 350, 400, 450 or 500 mg. The composition may be administered one or more times a day, for example 2, 3 or 4 times daily, so that the total daily dose for a 70 kg adult will normally be in the range 10 to 3000 mg. Such a dosage corresponds to approximately 0.15 to 50 mg/kg per day. Alternatively, in particular for injection, the unit dose will contain from 2 to 200 mg of a compound of the invention and be administered in multiples, if desired, to give the desired daily dose.

The present invention additionally provides a method of treating conditions in which degradation of connective tissue and other proteinaceous components of the body occurs, such as rheumatism and/or arthritic conditions in mammals, such as humans, which comprises administering to the mammal in need of such treatment an effective amount of a compound of formula (I) or a pharmaceutically acceptable salt thereof.

The present invention also provides the use of a compound of formula (I) or a pharmaceutically acceptable salt thereof, for the manufacture of a medicament for use in the treatment of conditions in which degradation of connective tissue and other proteinaceous components of the body occurs such as rheumatism and/or arthritic conditions.

The following Descriptions and Examples illustrate the preparation of compounds of the invention and the subsequent biological data illustrates their pharmacological activity. All temperatures are expressed in °C.

Description 1

N-(1-Phosphonoethyl)-leucine triethyl ester (D1)

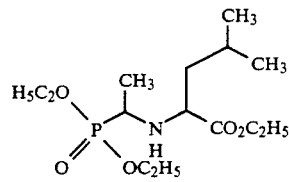

[1-[(Phenylmethyl)amino]ethyl]phosphonic acid, diethyl ester (2.76 g) [prepared by the procedure of F. R. Atherton et al. J. Med. Chem. 29, 29, 1986] was dissolved in ethanol (100 ml) and hydrogenated over 10% palladium on charcoal at atmospheric pressure. Ethyl (4-methyl-2-oxo)pentanoate (1.58 g) and molecular sieves were added and the hydrogenation continued for 48 h. The catalyst was removed by filtration and the filtrate evaporated in vacuo to yield a colourless oil, which was chromatographed on silica gel, eluting with ethyl acetate, to give the title compound as a mixture of isomers (0.83 g).

Description 2

N-(1-Diethoxyphosphinylethyl)-leucine (D2)

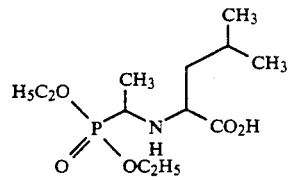

Method A

N-(1-Phosphonoethyl)-leucine triethyl ester (D1) (0.81 g) was dissolved in methanol (30 ml) and treated with sodium hydroxide (0.2 g) in water (15 ml). After 24 h, the solution was acidified with 4N HCl and extracted with dichloromethane. The organic extracts were dried over anhydrous sodium sulphate and the solvent removed in vacuo to give the title compound (0.66 g).

Method B

A solution of the hydrochloride salt of [1-(phenylmethyl)amino]ethyl]phosphonic acid diethyl ester (15 g) in ethanol (400 ml) was hydrogenated over 10% palladium on charcoal at atmospheric pressure until conversion to the primary amine was complete. 4-Methyl-2-oxopentanoic acid sodium salt was then added in the minimum volume of water and the hydrogenation continued for 3 days. The catalyst was removed by filtration and the filtrate evaporated in vacuo to give a colourless oil which was then taken up in chloroform and washed with water (30 ml) followed by dilute aqueous citric acid (2×30 ml) and a further aqueous wash. After drying (Na₂SO₄) the chloroform layer was evaporated to dryness to give the title compound as a sticky white solid having the same spectroscopic properties as the material obtained in Method A.

Description 3

N-[N-[N-(1-Diethoxyphosphinylethyl)-leucyl]-(S)-tryptophyl]-(S)-alanine, methyl ester (D3)

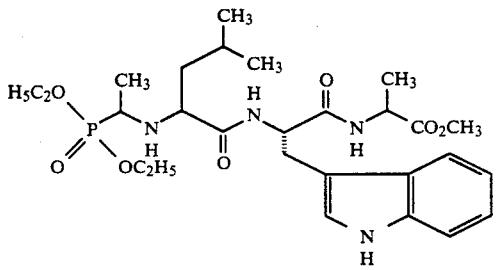

N-(1-Diethoxyphosphinylethyl)-leucine (D2) (1.0 g) in dichloromethane (50 ml) was cooled to 0° C. 1-Hydroxybenzotriazole (0.6 g) and 1-ethyl-3-(3-dimethylaminopropyl) carbodiimide hydrochloride (0.88 g) were added and the solution stirred at 0° C. for ½ hr. H-Trp-Ala-OMe trifluoroacetic acid salt (1.5 g) and diisopropylethylamine (2 ml) were added and the solution stirred at 0° C. for 1 h. After stirring at room temperature for 24 h, the solution was filtered, washed with water, saturated sodium bicarbonate and 10% citric acid solution and dried with anhydrous sodium sulphate. The solution was filtered and the solvent evaporated in vacuo to give a yellow oil. Purification by column chromatography on silica gel, eluting with 3% methanol/ethyl acetate gave the title compound (0.45 g) as a colourless oil.

Observed EI M+566.

Description 4

N-[N-[N-(1-Diethoxyphosphinylethyl)-leucyl]-O-methyl-(S)-tyrosyl]-(S)-alanine, methyl ester (D4)

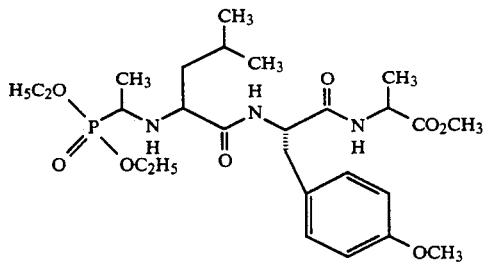

The title compound (0.45 g) was prepared from N-(1-diethoxyphosphinylethyl)leucine (D2) (0.5 g) and H-Tyr(Me)-Ala-OMe trifluoroacetic acid salt (0.84 g) by the procedure described in Description 3.

Observed EI M+557.

Description 5

N-((S)-1-Diethoxyphosphinylpropyl)-(R)-leucine, methyl ester and
N-((S)-1-Diethoxyphosphinylpropyl)-(S)-leucine, methyl ester (D5)

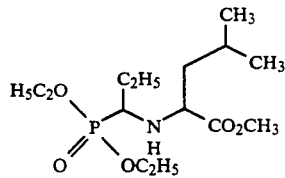

(S)-1'-[(1S,2S,5S)2-hydroxy-2,6,6-trimethylbicyclo[3,1,1]hep-3-ylidene amino]propylphosphonic acid diethyl ester (12 g) [prepared by the method of R. Jacquier et al. Phosphorus and Sulfur 36. 73, 1988] was stirred at room temperature for 72 h in a solution of 15% aqueous citric acid (210 ml) and tetrahydrofuran (245 ml). The solution was concentrated and washed with benzene (150 ml), basified with sodium carbonate and extracted with chloroform (4×200 ml). The combined organic extracts were dried with anhydrous sodium sulphate and the solvent removed in vacuo to give (S)-1-aminopropylphosphonic acid, diethyl ester (5.63 g) as a labile oil.

(S)-1-Aminopropylphosphonic acid, diethyl ester (5.63 g) and methyl (4-methyl-2-oxo)pentanoate (12.47 g) were dissolved in ethanol (200 ml) and hydrogenated over 10% palladium on charcoal at atmospheric pressure for 72 h. The catalyst was removed by filtration and the filtrate evaporated in vacuo to yield a colourless oil, which was dissolved in dichloromethane (50 ml), washed with saturated sodium bicarbonate solution (50 ml) and 5% aqueous citric acid (50 ml) and dried with anhydrous sodium sulphate. The removal of solvent gave the title compound, as a mixture of 2 diastereoisomers, which was chromatographed on silica gel, eluting with ether, to give a single diastereoisomer.

Isomer D5A (1.72 g [α]$_D^{20}$=+27.32° (c=1% in methanol).

δ (CDCl₃): 0.94 (6H, t), 1.06 (3H, t), 1.34 (6H, dt), 1.40-2.00 (5H, m), 2.68 (1H, m), 3.70 (3H, s), 3.78 (1H, t), 4.13 (4H, m).

Further elution gave a slower running single diastereoisomer.

Isomer D5B (1.26 g) [α]$_D^{20}$=+1.04° (c=1% in methanol).

δ (CDCl₃): 0.90 (6H, dd), 1.05 (3H, t), 1.45 (6H, dt), 1.42-1.95 (5H, m), 2.76 (1H, m), 3.48 (1H, t), 3.72 (3H, s), 4.12 (4H, m).

Description 6

N-((S)-1-Diethoxyphosphinylpropyl)-(R)-leucine and
N-((S)-1-Diethyoxyphosphinylpropyl)-(S)-leucine (D6)

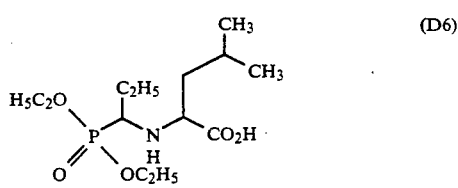

N-((S)-1-Diethoxyphosphinylpropyl)-(R or S)-leucine methyl ester (Isomer D5A)(1.71 g) was dissolved in ethanol (30 ml) and treated with sodium hydroxide (0.23 g) in water (20 ml). After 24 h, the solution was acidified with 5N HCl and extracted with dichloromethane. The organic extracts were dried over anhydrous sodium sulphate and the solvent removed in vacuo to give the title compound as a single diastereoisomer (D6A)(1.49 g).

$[\alpha]_D^{20}= +23.7°$ (c=1% in methanol).

$\delta$ (CDCl$_3$): 0.97(6H,d), 1.08(3H,t), 1.36(6H,dt), 1.44-1.99(5H,m), 2.80(1H,m), 3.78(1H,t), 4.17(4H,m). Observed M+309. C$_{13}$H$_{28}$NO$_5$P requires M 309.

Similarly, N-((S)-1-diethoxyphosphinylpropyl)-(R or S)-leucine methyl ester (Isomer D5B)(1.24 g) gave the title compound as a single diastereoisomer (D6B) (1.05 g).

$[\alpha]_D^{20}+4.07°$ (c=0.984% in methanol).

$\delta$ (CDCl$_3$): 0.96(6H,dd), 1.05(3H,t), 1.34(6H,dt), 1.43-1.98(5H,m), 2.78(1H,dt), 3.42(1H,dd), 4.16(4H,m). Observed M+309. C$_{13}$H$_{28}$NO$_5$P requires M 309.

Description 7

3-[N-[N-((S)-1-Phosphonopropyl)-(R)-leucyl]]-(−)-aminoazacyclotridecan-2-one, diethyl ester and 3-[N-[N-((S)-1-phosphonopropyl-(S)-leucyl]]-(−)-aminoazacyclotridecan-2-one, diethyl ester (D7)

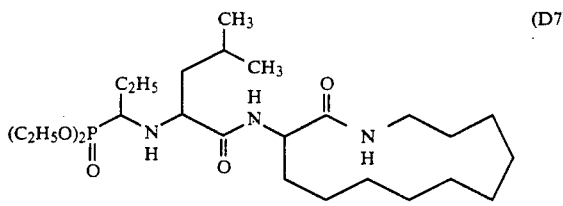

N-((S)-1-Diethoxyphosphinylpropyl)-(R or S)-leucine (D6A) (0.68 g) in dichloromethane (25 ml) was cooled to 0° C. 1-Hydroxybenzotriazole (0.41 g) and 1-ethyl-3(3-dimethylaminopropyl)carbodiimide hydrochloride (0.58 g) were added and the solution stirred at 0° C. for ½ h. (−)-3-Aminoazacyclotridecan-2-one (0.52 g) ($[\alpha]_D^{20}= -63.6°$ (c=1% in methanol)) in dichloromethane (25 ml) was added dropwise. The solution was stirred at room temperature for 24 h, washed with water, saturated sodium bicarbonate and 5% aqueous citric acid. The solution was dried with anhydrous sodium sulphate and evaporated in vacuo to give a colourless oil. Purification by column chromatography on silica gel, eluting with a gradient of 2-10% methanol/ether gave a single diastereoisomer.

Isomer D7A (0.83 g) $[\alpha]_D^{20}= -6.23°$ (c=1% in methanol) m.p. 146°-147° C.

$\delta$ (CDCl$_3$): 0.94(6H,t), 1.12(3H,t), 1.26-1.97(30H,m), 2.68(1H,m), 2.87(1H,m), 3.68(2H,m), 4.13(4H,m), 4.40 (1H,m), 6.47(1H,broad s), 7.62(1H,d).

Analysis: C$_{25}$H$_{50}$N$_3$O$_5$P requires C,59.62; H,10.01; N,8.34%. Found C,59.78; H,10.24; N,8.38%.

Further elution gave a slower running single diastereoisomer as a minor impurity.

Isomer D7B (0.20 g) $[\alpha]_D^{20} = -82.11°$ (c=1% in methanol) m.p. 142°-144° C.

$\delta$ (CDCl$_3$): 0.88(6H,dd), 1.04(3H,t), 1.14-1.91(30H,m), 2.68(2H,m), 3.55(1H,m), 3.70(1H,m), 4.06(4H,m), 4.43 (1H,m), 6.97(1H,broad s), 7.69(1H,dd).

Analysis: C$_{25}$H$_{50}$N$_3$O$_5$P requires, C,59.62; H,10.01; N,8.34%. Found: C,59.61; H,10.06; N,8.10%.

Similarly, N-((S)-1-diethoxyphosphinylpropyl)-(R or S)-leucine (D6B) (0.64 g) gave the title compound as a single diastereoisomer (D7C) (0.39 g).

$[\alpha]_D^{20} = -33.99°$ (c=1% in methanol).

$\delta$ (CDCl$_3$): 0.96(6H,d), 1.03(3H,t), 1.20-1.92(30H,m), 2.75(1H,dt), 2.93(1H,m), 3.32(1H,m), 3.54(1H,m), 4.17 (4H,m), 4.47(1H,dt), 7.74(1H,broad s), 8.11(1H,d). Observed M+503. C$_{25}$H$_{50}$N$_3$O$_5$P requires M 503.

Description 8

Dibenzyl (1-hydroxypropyl)phosphonate (D8)

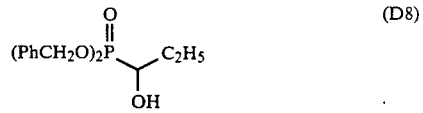

The general method of F. Texier-Boullet and A. Foucaud [Synthesis, 1982, 916] was employed. A mixture of dibenzyl phosphite (31.13 ml, 0.14 mole) and propionaldehyde (10.21 ml, 1 equiv.) was stirred at room temperature and basic alumina (70 g) added in one portion. After standing overnight at room temperature chloroform was added and the alumina collected and washed with chloroform. The filtrate was evaporated to dryness and the resulting clear oil chromatographed on silica gel (600 g) with gradient elution (ether—5% methanol/ether). The title compound was obtained as a clear oil which solidified on standing (27.82 g, 64%). A sample was recrystallized from ether/pentane to give a white crystalline solid, m.p. 81°-82° C.

Found: C,64.09; H,6.71. C$_{17}$H$_{21}$O$_4$P$_1$ requires C,63.74; H,6.61%.

$\delta$ (CDCl$_3$) 1.04(3H,t,J=7Hz), 1.6-1.95(2H,m), 2.27(1H, brs), 3.8(1H, 2 overlapping triplets, J=5 and 10 Hz), 4.97-5.18(4H,m), 7.34(10H,s).

Description 9

Dibenzyl ((1-trifluoromethanesulphonyloxy)propyl)phosohonate (D9)

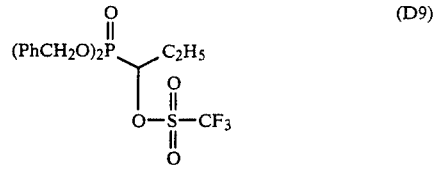

The title compound was prepared by the general method of E. Vedejs et al. [J. Org. Chem. 1985, 50(12), 2165]. A solution of dibenzyl (1-hydroxypropyl)phosphonate (D8) (24.97 g, 0.078 mole) in methylene chloride (180 ml) was cooled to −50° C. under N$_2$. 2,6-Lutidine (11.12 ml, 0.095 mole) was added followed by trifluoromethanesulphonic anhydride (15.1 ml, 0.0898 mole) keeping the temperature at −50° C. The mixture was allowed to warm slowly to 0° C. and then taken into cold ether. The solution was subjected to a rapid aqueous work-up by washing the organic layer with ice-cold water, dilute hydrochloric acid (×2) and finally brine. The organic layer was dried (anhydrous MgSO$_4$) and evaporated to dryness to give the title compound as a pinkish orange oil (33.77 g, 96%) which was used without further purification.

δ (CDCl₃) 1.08(3H,t,J=7Hz), 1.88(2H,m), 4.94(1H, 2 overlapping triplets, J=5.5 and 7 Hz), 4.88–5.22(4H,m) and 7.35(10H,m).

Description 10

(S)-Leucyl-(−)-3-aminoazacyclotridecan-2-one (D10)

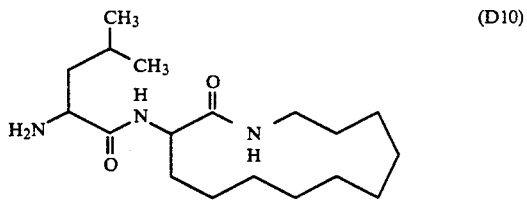

(D10)

N-Benzyloxycarbonyl-(S)-leucine (1.87 g) in dichloromethane (130 ml) was cooled to 0° C. 1-Hydroxybenzotriazole (1.25 g) and 1-ethyl-3(3-dimethylaminopropyl))carbodiimide hydrochloride (1.88 g) were added and the solution stirred at 0° C. for ½ h. (−)-3-Aminoazacyclotridecan-2-one (1.5 g) ([α]$_D^{20}$=−63.6° (c=1% in methanol)) in dichloromethane (50 ml) was added dropwise. The solution was stirred at room temperature for 24 h, washed with water, saturated sodium bicarbonate and dried with anhydrous sodium sulphate. The solution was filtered and the solvent evaporated in vacuo to give a white solid which was dissolved in ethanol (100 ml) and hydrogenated over 10% palladium on charcoal at atmospheric pressure. The solution was filtered and solvent evaporated in vacuo to give the title compound (D10) (1.1 g).

δ (CDCl₃): 0.95(6H,t), 1.20–2.10(23H,m), 2.83(1H,m), 3.40(1H,m), 3.73(1H,m), 4.45(1H,m), 6.68(1H,broad s) and 7.96(1H,broad d).

Observed M+325. C₁₈H₃₅N₃O₂ requires M 325.

Description 11

3-[N-[N-(1-Phosphonopropyl)-(S)-leucyl]]-(−)-aminoazacyclotridecan-2-one, dibenzyl ester (D11)

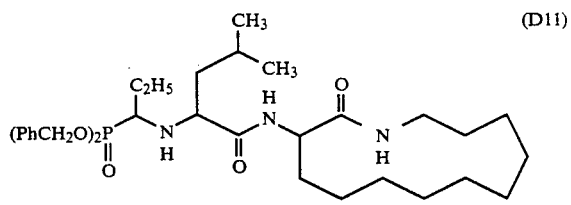

(D11)

Dibenzyl 1-(trifluoromethanesulphonyloxy)propyl-phosphonate (D9) (1.4 g) and (S)-leucyl-(−)-3-aminoazacyclotridecan-2-one (D10) (1.0 g) were dissolved in methanol (6 ml). 1,8-Bis(dimethylamino)-naphthalene (0.66 g) was added and the reaction mixture stirred at room temperature for ten days with light excluded. The solvent was evaporated in vacuo and the residue dissolved in chloroform (50 ml), washed with water, dilute citric acid solution and dried over anhydrous sodium sulphate. The removal of solvent gave an orange oil which was chromatographed on silica gel, eluting with ethyl acetate, to give the title compound as a mixture of two diastereoisomers (D11) (0.73 g).

Observed FAB (M+H)+628. C₃₅H₅₄N₃O₅P requires M 627.

Description 12

N-(1-(R)-Dibenzyloxyphosphinylpropyl)-(S)-leucine (D12A) and
N-(1-(S)-Dibenzyloxyphosphinylpropyl)-(S)-leucine (D12B)

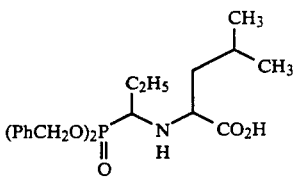

Method A

Following the general method of U.S. 4808-741A for the preparation of leucine trimethylsilyl ester a mixture of (S)-leucine (1.15 g, 0.0088 mole), hexamethyldisilazane (1.75 ml), and triethylamine (1.38 ml) in acetonitrile (13.5 ml) was heated at reflux for a total of 4h.

Dibenzyl ((1-trifluoromethanesulphonyloxy)propyl)-phosphonate (D9) (4.5 g, 0.01 mole) was then added and the mixture maintained at 40°–42° C. for 48h. The reaction can also be carried out at ambient temperature. After cooling the mixture was filtered, washed with methanol and the filtrate evaporated to dryness. The residue was taken up in chloroform and washed with dilute HCl (×2) and finally water. The chloroform layer was dried (anhydrous Na₂SO₄), filtered and evaporated to dryness to give an orange gummy solid (3.67 g). The crude product was triturated with the minimum volume of ether/pentane to give a white crystalline solid which after collection, washing with a little cold ether/pentane and drying gave the title compound, R,S isomer (D12A) (0.47 g, 11%), m.p. 112°–115° C.

Observed Desorption CI (NH₃) MH+434. C₂₃H₃₂NO₅P requires M 433.

[α]$_D^{20}$−23.09° (c=0.97 MeOH).

Found: C,63.73; H,7.42; N,3.23. C₂₃H₃₂NO₅P requires C,63.73; H,7.44; N,3.23%.

δ (CDCl₃): 0.89 (6H,t), 1.03 (3H,t), 1.25–2.0 (5H,m), 2.74 (1H,m), 3.28 (2H, brs), 3.73 (1H, brt), 4.9–5.15 (4H, m), 7.35 (10H, s).

The other isomer, N-(1-(S)-dibenzyloxyphosphinylpropyl)-(S)-leucine (D12B), can be obtained by preparative HPLC using a Hamilton PRP-1 column, 300×7.0 mm, 264R with a 40:60 acetonitrile:water eluent mixture and a flow rate of 4.0 ml/min. Under these conditions the R,S isomer (D12A) elutes first with a retention time of 34.6 min and the S,S isomer (D12B) is well separated at 42.7 min.

For the isomer (D12B): Observed FAB (M+H)+434. C₂₃H₃₂NO₅P requires M 433.

δ (CDCl₃) 0.85 (6H,t), 0.92 (3H,t), 2.62 (1H,m), 3.26 (1H,m), 4.8–5.1 (4H,m), 7.28 (10H,s). There are in addition signals in the region of 1.5 δ which are hidden by an overlapping water signal.

The S,S isomer (D12B) on coupling with (S)-amino acid derivatives leads to the S,S,S series.

Method B

A mixture of (S)-leucine methyl ester hydrochloride (0.543 g; 0.003 mole), dibenzyl (1-trifluoromethanesulphonyloxy)propyl)-phosphonate (D9) (1.35 g; 0.003 mole) and anhydrous potassium carbonate (1.0 g) in methanol (2 ml) was heated at 50° C., with stirring, for 4 hours and then left at room temperature overnight.

The reaction mixture was evaporated to dryness in vacuo, and dissolved in chloroform (5 ml) and filtered. The filtrate, and washings, were combined and chromatographed on silica gel 60 (50 g) using ethyl acetate-pentane (1:1) as the eluent, to afford a mixture of N-(1-(R)-dibenzyloxyphosphinylpropyl)-(S)-leucine methyl ester and N-(1-(S)-dibenzyloxyphosphinylpropyl)-(S)-leucine methyl ester as an oil (0.55 g).

The above mixture of esters (1.1 g, 0.0025 mole) in methanol (4.0 ml) was treated with a solution of sodium hydroxide (0.11 g; 0.00275 mole) in water (1.5 ml), and the solution was stirred at room temperature overnight. It was evaporated to one third volume, in vacuo, taken in water and extracted with ether. The aqueous fraction was acidified with citric acid to pH 3–4 and then extracted (5×) with chloroform. The chloroform fraction was dried ($Na_2SO_4$) and evaporated to dryness in vacuo to give a mixture of the title compounds (D12A) and (D12B) as an oil that slowly solidified.

Trituration of the product with ether gave N-(1-(R)-dibenzyloxyphosphinylpropyl)-(S)-leucine (D12A) (0.34 g) as a white crystalline solid, identical to the product obtained by Method A.

Description 13

N-[N-(1-(R)-Phosphonopropyl)-(S)-leucyl]-O-methyl-(S)-tyrosin-N-(2-hydroxylethyl)amide, dibenzyl ester (D13)

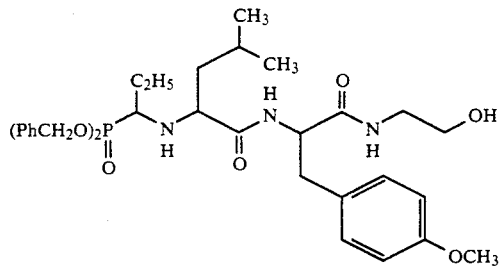

A stirred solution of N-(1-(R)-dibenzyloxyphosphinylpropyl-(S)-leucine (D12A) (0.89 g, 0.0021 mole) in acetonitrile (9 ml) was cooled to 0° C. in an ice-bath under nitrogen and 1,1'-carbonyldiimidazole (0.37 g, 1.1 equiv.) added in one portion. After 15 min the mixture was allowed to warm to room temperature over 30 min and then recooled to 0° C. After a further 15 min O-methyl-(S)-tyrosin(2-hydroxymethyl)amide[1] [prepared from Boc-O-methyl-(S)-tyrosine by standard coupling procedures and deprotection with $TFA/CH_2Cl_2$] (0.49 g, 1 equiv.) was added and the mixture stirred overnight at room temperature. The reaction mixture was then evaporated to dryness and the residue partitioned between EtOAc and water. The organic layer was washed successively with saturated $NaHCO_3$, citric acid, water, and brine. The organic layer was dried (anhydrous $Na_2SO_4$) and evaporated to dryness to give a pale yellow gum (1.16 g). Chromatography on silica gel with gradient elution (EtOAc rising to 10% MeOH/EtOAc) gave a colourless gum (0.43 g, 32%).

[1]. U.S. Pat. No. 2,833,764

Observed FAB $(M+H)^+$ 654. $C_{35}H_{48}N_3O_7P$ requires 653.

δ ($CDCl_3$) 0.8 (6H, 2 overlapping d), 0.96 (3H,t), 1.05–1.35 (2H,m), 1.35–1.65 (2H,m), 1.65–1.9 (1H,m), 2.4 (1H, brs), 2.68 (1H,m), 2.9 (1H, 2 overlapping d), 3.07 (1H, 2 overlapping d), 3.2–3.45 (2H,m), 3.5–3.8 (total 6H, m; including singlet at 3.2 (3H)), 4.72 (1H,dd), 4.83–5.1 (4H,m), 6.75 (2H,d), 7.08 (2H,d), 7.2 (1H, brt), 7.3 (10H,s), 7.5 (1H,d).

Description 14

Dibenzyl (1-hydroxypentyl)phosphonate (D14)

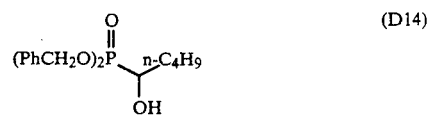

The general method of F. Texier-Boullet and A. Foucaud [Synthesis, 1982, 916] was employed. A mixture of dibenzyl phosphite (7.73 ml, 0.035 mole) and valeraldehyde (11.15 ml, 0.105 mole) was stirred at room temperature and basic alumina (35 g) added in one portion. After standing overnight at room temperature chloroform was added and the alumina collected and washed with chloroform. The filtrate was evaporated to dryness and the resulting oil chromatographed on silica gel with gradient elution (50% pentane/ethyl acetate-ethyl acetate) to give the title compound as a colourless oil (9.17 g, 76%).

δ ($CDCl_3$) 0.86 (3H,t), 1.20–1.80 (6H,m), 2.60 (1H,brs), 3.87 (1H, 2 overlapping triplets), 5.06 (4H,m), 7.34 (10H,s).

Description 15

Dibenzyl ((1-trifluoromethanesulphonyloxy)pentyl)phosphonate (D15)

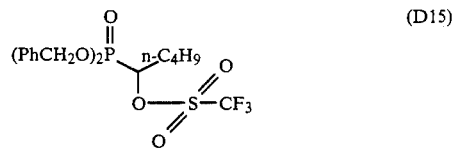

The title compound was prepared from dibenzyl (1-hydroxypentyl)phosphonate (D14) by the method described in Description 9.

δ ($CDCl_3$) 0.88 (3H,t), 1.18–2.00 (6H,m), 5.03 (5H,m), 7.32 (10H,m).

Description 16

3-[N-[N-(1-Phosphonopentyl)-(S)-leucyl]]-(−)-aminoazacyclotridecan-2-one, dibenzyl ester (D16)

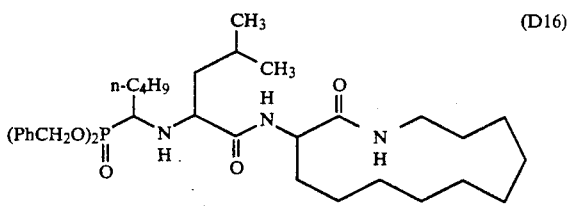

Dibenzyl 1-(trifluoromethanesulphonyloxy)pentylphosphonate (D15) (0.96 g) and (S)-leucyl-3-(−)-aminoazacyclotridecan-2-one (D10) (0.65 g) were dissolved in methanol (2.5 ml). 1,8-Bis(dimethylamino)naphthalene (0.426 g) was added and the reaction mixture stirred at room temperature for ten days with light excluded. The solvent was evaporated in vacuo and the residue dissolved in chloroform (50 ml), washed with water, dilute citric acid solution and dried over anhydrous sodium sulphate. The removal of solvent gave an orange oil which was chromatographed on silica gel, eluting with ethyl acetate, to give the title compound as a mixture of two diastereoisomers (D16) (0.4 g, 30%).

Observed FAB (M+H)+ 656. $C_{37}H_{58}N_3O_5P$ requires M 655.

EXAMPLE 1

N-[N-[N-(1-Phosphonoethyl)-leucyl]-(S)-tryptophyl]-(S)-alanine, methyl ester (E1)

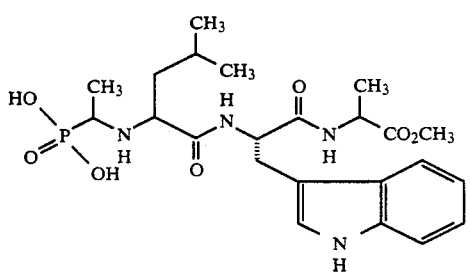

The diethyl ester (D3) (0.2 g) was dissolved in dichloromethane (10 ml) and treated with bromotrimethylsilane (0.5 ml). The solution was stirred at room temperature for 4 days, methanol (20 ml) was added and the solvent evaporated in vacuo to give the crude product. Column chromatography on reverse phase silica, eluting with a gradient of 5% to 30% methanol in water, gave the title compound (0.1 g) as a mixture of diastereoisomers.

Observed FAB (M+H)+ 511. $C_{23}H_{35}N_4O_7P$ requires M 510.

EXAMPLE 2

N-[N-[N-(1-Phosphonoethyl)-leucyl]-O-methyl-(S)-tyrosyl]-(S)-alanine, methyl ester (E2).

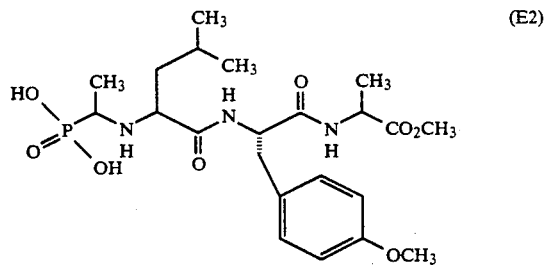

The title compound (0.1 g) was prepared from D4 (0.25 g) by the method described in Example 1.

δ (CD₃OD): 0.83(6H,m), 1.05-1.60(9H,m), 2.38-3.30(4H,m), 3.65-3.78(6H,m), 4.40(1H,m), 4.60(1H,m), 6.83(2H,m), 7.18(2H,m).

Observed FAB (M+H)+ 502. $C_{22}H_{36}N_3O_8P$ requires M 501.

EXAMPLE 3

3-[N-[N-((S)-1-Phosphonopropyl)-(R)-leucyl]]-(−)-aminoazacyclotridecan-2-one and 3-[N-[N-((S)-1-Phosphonopropyl)-(S)-leucyl]]-(−)-aminoazacyclotridecan-2-one (E3)

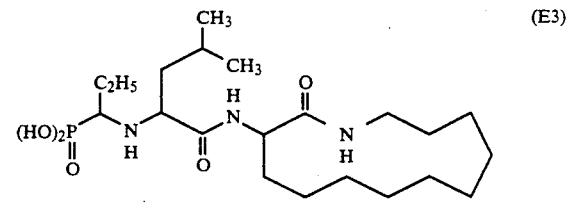

Method A

The diethyl ester (D7A) (0.78 g) was dissolved in dichloromethane (30 ml) and treated with bromotrimethylsilane (2.04 ml). The solution was stirred at room temperature for 72 h, methanol (20 ml) and water (10 ml) were added and the solution evaporated in vacuo to give a white solid (E3A).

Observed FAB (M+H)+ 448. $C_{21}H_{42}N_3O_5P$ requires M 447.

Similarly, the diethyl ester (D7C) (0.23 g) gave the title compound as a single diastereoisomer (E3C).

$[α]_D^{20} = -58.75°$ (c=1% in methanol).

m.p. 180°–183° C.

δ (CD₃OD): 0.97(6H,dd), 1.12 (3H,t), 1.25–1.93(23H,m), 2.79(1H,m), 2.97(1H,m), 3.66(1H,m), 4.22(1H,m), 4.40(1H,dd).

Observed FAB (M+H)+ 448. $C_{21}H_{42}N_3O_5P$ requires M 447.

Method B

The dibenzyl ester (D11) (0.19 g) was dissolved in ethanol (100 ml) and hydrogenated over 10% palladium on charcoal at atmospheric pressure for 24 h. The solution was filtered and solvent evaporated in vacuo to give a mixture of two diastereoisomers which were separated by hplc [Hamilton PRP-1 column (300×7mm); mobile phase, acetonitrile/water (17.5/8.25)+0.1% TFA; flow rate, 6 ml/min.] to give a single diastereoisomer (E3C) with retention time 32 minutes.

From the two methods of preparation A and B it would appear that isomer E3C is 3-[N-[N-((S)-1-phosphonopropyl)-(S)-leucyl]]-(−)-aminoazacyclotridecan-2-one. Therefore isomer E3A must be 3-[N-[N-((S)-1-phosphonopropyl)-(R)-leucyl]]-(−)-aminoazacyclotridecan-2-one.

Coupling of (D12B) with (−)-3-aminoazacyclo-tridecan-2-one followed by hydrogenation at atmospheric pressure with 10% palladium on charcoal provides an alternative route to 3-[N-[N-((S)-1-phosphonopropyl)-(S)-leucyl]]-(−)-aminoazacyclotridecan-2-one (E3C).

EXAMPLE 4

3-[N-[N-((R)-1-Phosphonopropyl)-(S)-leucyl]]-(—)-aminoazacyclotridecan-2-one (E4)

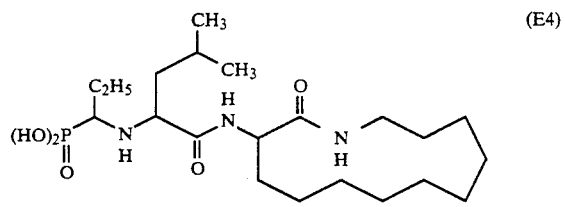

The dibenzyl ester (D11) (0.19 g) was dissolved in ethanol (100 ml) and hydrogenated over 10% palladium on charcoal at atmospheric pressure for 24 h. The solution was filtered and solvent evaporated in vacuo to give a mixture of two diastereoisomers E3C and E4 which were separated by hplc [Hamilton PRP-1 column (300×7mm); mobile phase, acetonitrile/water (17.5/8.25)+0.1% TFA; flow rate, 6 ml/min.] to give a single diastereoisomer (E4) with retention time 37 minutes.

δ (CD$_3$OD): 1.00(6H,t), 1.11(3H,t), 1.24–2.13(23H,m), 2.74(2H,m), 3.64(1H,m), 4.32(1H,m), 4.53(1H,t).

Observed FAB (M+H)$^+$ 448. $C_{21}H_{42}N_3O_5P$ requires M 447.

Isomer E4 differs from isomer E3C in having the opposite configuration at the chiral centre adjacent to phosphorus. It would therefore appear that isomer E4 is 3-[N-[N-((R)-1-phosphonopropyl)-(S)-leucyl]]-(—)-aminoazacyclotridecan-2-one.

EXAMPLE 5

N-[N-(1-(R)-Phosphonopropyl)-(S)-leucyl]-O-methyl-(S)-tyrosin-N-(2-hydroxyethyl)amide (E5)

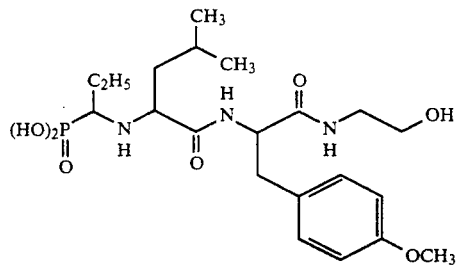

A solution of N-[N-(R)-phosphonopropyl)-(S)-leucyl]-O-methyl-(S)-tyrosin-N-(2-hydroxyethyl)amide, dibenzyl ester (D13) (206 mg, 0.00032 mole) in methanol with 10% palladium on charcoal (50 mg) was hydrogenated at atmospheric pressure. The catalyst was collected and washed with methanol and the filtrate evaporated to dryness. The residue was dissolved in water, filtered and freeze-dried to give a white solid (120 mg).

Observed dynamic FAB (M+H)$^+$ 474. $C_{21}H_{36}N_3O_7P$ requires M 473.

Single peak at retention time 18.57 min on HPLC [RP Select B, 125×4 mm, 394R with mobile phase 5:95 acetonitrile: 0.05M aqueous phosphate (pH 2.5), flow rate 2 ml/min].

EXAMPLE 6

3-[N-[N-((S)-Phosphonopropyl)-(S)-leucyl]]-(—)-aminoazacyclotridecan-2-one, monoethyl ester sodium salt (E6)

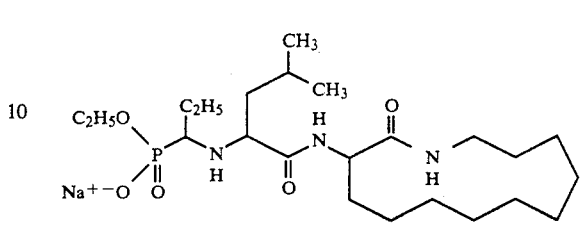

The diethyl ester (D7C) (0.015 g) was dissolved in methanol (3 ml) and treated with an excess of sodium hydroxide in water for 5 days at room temperature. The solvent was evaporated in vacuo to give a white solid which was purified by column chromatography using reverse-phase silica eluting with a gradient of 5% to 10% methanol in water to give the title compound (0.01 g).

Observed FAB (M+H)$^+$ 476, (M+Na$^+$) 498. $C_{23}H_{46}N_3O_5P$ requires M 475.

δ (CD3OD) 0.88 (6H,t), 0.96 (3H,t), 1.20–1.90 (28H,m), 2.52 (1H,m), 2.98 (1H,m), 3.43 (2H,m), 3.90 (2H,m), 4.22 (1H,m).

EXAMPLE 7

3-[N-[N-(1-Phosphonopropyl)-(S)-leucyl]]-(—)-aminoazacyclotridecan-2-one, disodium salt (E7)

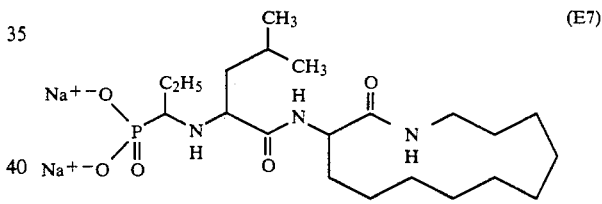

The title compound was prepared from the mixture of two diastereoisomers produced in Example 4 (prior to their separation by HPLC). The mixture of isomers (709 mg, 0.0016 mole) in water (150 ml) was cooled in an ice-bath with stirring and treated with sodium hydroxide solution (10%, 1.26 ml, 2 equivalents). The resulting solution was filtered and freeze-dried to give the title compound as a white solid (746 mg, 96%).

EXAMPLE 8

3-[N-[N-(1-Phosphonopentyl)-(S)-leucyl]]-(—)-aminoazacyclotridecan-2-one (E8)

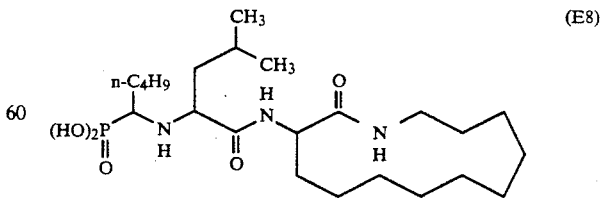

The dibenzyl ester (D16) (0.4 g) was dissolved in ethanol (100 ml) and hydrogenated over 10% palladium on charcoal at atmospheric pressure for 24h. The solution was filtered and solvent evaporated in vacuo to give the title compound as a mixture of two diastereoisomers (0.28 g).

Observed FAB (M+H)+ 476. $C_{23}H_{46}N_3O_5P$ requires M 475.

COLLAGENASE INHIBITOR ASSAY

The test is performed essentially as in Cawston and Barrett Anal. Biochem. 99, 340–345 (1979). Compounds for testing are dissolved in methanol and added to purified rabbit bone collagenase or human collagenase purified from culture supernatants from the human lung fibroblast cell line, WI-38, diluted in a suitable aqueous buffer. After a 5 min pre-incubation at 37° C., the assay tubes are cooled to 4° C. and $^{14}C$-acetylated rat skin Type I collagen is added. The assay tubes are incubated at 37° C. overnight. The $^{14}C$-collagen forms insoluble fibrils which are the substrate for the enzyme.

To terminate the assay, the assay tubes are spun at 12000 rpm for 25 min. Undigested $^{14}C$-collagen remains as insoluble fibrils and is pelleted, while digested $^{14}C$-collagen remains as soluble peptides in the supernatant. A sample of the supernatant is taken for liquid scintillation counting.

The activity of collagenase inhibitors (IC$_{50}$: 50% inhibitory concentration) is expressed as the concentration of compound that inhibits a known (standard) concentration of enzyme by 50%, or as the % inhibition of the collagen degradation caused by the known (standard) concentration of enzyme, at a stated concentration of the compound.

The activities of representative compounds of the invention, in the test procedure, are illustrated in the tables below.

| Inhibition of rabbit bone collagenase | | |
|---|---|---|
| Example No. | Isomer | IC$_{50}$ (μM) |
| E1 | Mixture of diastereoisomers | 2.4 |
| E2 | Mixture of diastereoisomers | 3.1 |

| Inhibition of human lung fibroblast collagenase | | |
|---|---|---|
| Example No. | Isomer | IC$_{50}$ (μM) |
| E3C | S,S,(−) | 0.045 |
| E4 | R,S,(−) | 0.166 |
| E8 | R,S,(−) and S,S,(−) | 9.49 |

We claim:

1. A compound of formula (I) or a pharmaceutically acceptable salt thereof:

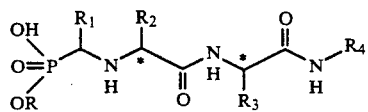

in which,
R is hydrogen, C$_{1-6}$ alkyl or optionally substituted benzyl of the group in which the phenyl moiety is optionally substituted by a moiety selected from —OH, C$_{1-6}$ alkyl, C$_{1-6}$ alkoxy, halogen, —NHCO C$_{1-6}$ alkyl, —NHCOPh and —CONR$_5$R$_6$;

R$_1$ is hydrogen or C$_{1-6}$ alkyl;

R$_2$ is C$_{3-6}$ alkyl;

R$_3$ is hydrogen, C$_{1-8}$ alkyl, —CH—Z where Z is a phenyl group or a indolyl group, said phenyl or indolyl group optionally substituted by a moiety selected from —OH, C$_{1-6}$ alkyl, C$_{1-6}$ alkoxy, halogen, —NHCO C$_{1-6}$ alkyl, —NHCOPh and —CONR$_5$R$_6$, or R$_3$ is a group

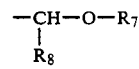

where R$_7$ is hydrogen, alkyl or —CH$_2$—Ph where Ph is a phenyl group optionally substituted by a moiety selected from —OH, C$_{1-6}$ alkyl, C$_{1-6}$ alkoxy, halogen, —NHCO C$_{1-6}$ alkyl, —NHCOPh and —CONR$_5$R$_6$ and R$_8$ is hydrogen or C$_{1-8}$ alkyl; and R$_4$ is —CH$_2$—(CH$_2$)$_n$OR$_5$ or —CH$_2$—(CH$_2$)$_n$OCOR$_6$ or

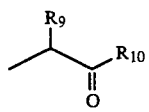

where n is an integer from 1 to 6; R$_5$, R$_6$, and R$_9$ are hydrogen or C$_{1-6}$ alkyl; and R$_{10}$ is hydroxy or —O—C$_{1-6}$ alkyl or —NR$_5$R$_6$, where R$_5$ and R$_6$ may be linked to form an indolyl group which may be unsubstituted or substituted by C$_{1-6}$ alkyl, phenyl, or benzyl; or R$_3$ and R$_4$ are joined together as —(CH$_2$)$_m$— where m is an integer from 4 to 12.

2. A compound according to claim 1, in which R is hydrogen, methyl or ethyl.

3. A compound according to claim 1 in which R$_1$ is hydrogen, methyl, ethyl, isopropyl or n-butyl.

4. A compound according to claim 1 in which R$_2$ is n-butyl, iso-butyl or sec-butyl.

5. A compound according to claim 1 in which R$_3$ is benzyl, 4-hydroxybenzyl, 4-methoxybenzyl or 3-indolylmethyl and R$_4$ is —(CH$_2$)$_2$OH, —(CH$_2$)$_{20}$CH$_3$ or —CH(CH$_3$)CO$_2$CH$_3$; or R$_3$ and R$_4$ are combined as —(CH$_2$)$_m$ where m is 10.

6. A compound according to claim 1 in which R is hydrogen or ethyl; R$_1$ is methyl, ethyl or n-butyl; R$_2$ is iso-butyl; R$_3$ is 4-methoxybenzyl or 3-indolylmethyl and R$_4$ is —(CH$_2$)$_2$OH or —CH(CH$_3$)CO$_2$CH$_3$; or R$_3$ and R$_4$ together are —(CH$_2$)$_m$ where m is 10.

7. A compound according to claim 1 in which the chiral centres marked with an asterisk in formula (I) have the S-configuration when R$_3$ is other than hydrogen.

8. A compound selected from the group comprising:
N-[N-[N-(1-phosphonoethyl)-leucyl]-(S)-tryptophyl]-(S)-alanine, methyl ester;
N-[N-[N-(1-phosphonoethyl)-leucyl]-O-methyl-(S)-tyrosyl]-(S)-alanine, methyl ester;
3-[N-[N-((S)-1-phosphonopropyl)-(R)-leucyl]]-(−)-aminoazacyclotridecan-2-one.
3-[N-[N-((S)-1-phosphonopropyl)-(S)-leucyl]]-(−)-aminoazacyclotridecan-2-one;
3-[N-[N-((R)-1-phosphonopropyl)-(S)-leucyl]-(−)-aminoazacyclotridecan-2-one;
N-[N-(1-(R)-phosphonopropyl)-(S)-leucyl]-O-methyl-(S)-tyrosin-((2-hydroxyethyl)amide;
3-[N-[N-((S)-phosphonopropyl)-(S)-leucyl]]-(−)-aminoazacyclotridecan-2-one, monoethyl ester, sodium salt;
3-[N-[N-(1-phosphonopropyl)-(S)-leucyl]]-(−)-aminoazacyclotridecan-2-one, disodium salt; and 3    -[N-[N-(1-phosphonopentyl)-(S)-leucyl]]-(−)-aminoazacyclotridecan-2-one.

9. A pharmaceutically acceptable salt of a compound according to any one of claims 1 to 8.

10. A process for the preparation of a compound of formula (I) as defined in claim 1, which process comprises converting a group $R_{20}$ to hydrogen by cleaving a group $R_{20}$ from a compound of formula (II):

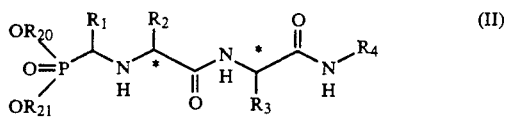

in which $R_{20}$ is alkyl or optionally substituted benzyl, and $R_{21}$ is hydrogen, alkyl or optionally substituted benzyl, and $R_1$, $R_2$, $R_3$ and $R_4$ are as defined for formula (I) in claim 1, and where necessary, converting $R_{21}$ to hydrogen.

11. A compound selected from the group comprising:
N-[N-[N-(1-diethoxyphosphinylethyl)-leucyl]-(S)-tryptophyl]-(S)-alanine, methyl ester;
N-[N-[N-(1-diethoxyphosphinylethyl)-leucyl]-O-methyl-(S)-tyrosyl]-(S)-alanine, methyl ester;
3-[N-[N-(S)-1-phosphonopropyl)-(R)-leucyl]]-(−)-aminoazacyclotridecan-2-one, diethyl ester;
3-[N-[N-((S)-1-phosphonopropyl-(S)-leucyl]]-(−)-aminoazacyclotridecan-2-one, diethyl ester;
3-[N-[N-(1-phosphonopropyl)-(S)-leucyl]]-(−)-aminoazacyclotridecan-2-one, dibenzyl ester;
N-[N-(1-(R)-Phosphonopropyl)-(S)-leucyl]-O-methyl-(S)-tyrosin-N-(2-hydroxylethyl)amide, dibenzyl ester; and
3-[N-[N-(1-phosphonopentyl)-(S)-leucyl]]-(−)-aminoazacyclotridecan-2-one, dibenzyl ester.

12. A compound of formula (II):

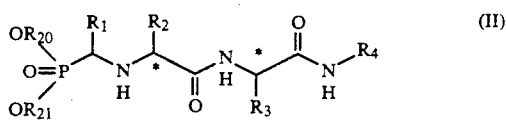

in which $R_{20}$ is alkyl or optionally substituted benzyl, and $R_{21}$ is hydrogen, alkyl or optionally substituted benzyl, and $R_1$, $R_2$, $R_3$ and $R_4$ are as defined for formula (I) in claim 1.

13. The compound of formula (II) as defined in claim 12, wherein $R_{21}$ is not hydrogen.

14. A pharmaceutical composition comprising a compound of formula (I) as defined in claim 1, or a pharmaceutically acceptable salt thereof, and a pharmaceutically acceptable carrier.

15. A method of treating conditions in which degradation of connective tissue and other proteinaceous components of the body occurs, in mammals, which method comprises administering an effective amount of a compound of formula (I) as defined in claim 1 or a pharmaceutically acceptable salt thereof to a sufferer.

* * * * *